US00PP24507P3

(12) United States Plant Patent
Pavlich et al.

(10) Patent No.: US PP24,507 P3
(45) Date of Patent: May 27, 2014

(54) *HEUCHERA* PLANT NAMED 'GEORGIA PLUM'

(50) Latin Name: ***Heuchera* hybrid**
Varietal Denomination: Georgia Plum

(75) Inventors: John C. Pavlich, Olympia, WA (US); Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 182 days.

(21) Appl. No.: 13/507,438

(22) Filed: Jun. 27, 2012

(65) Prior Publication Data

US 2014/0007311 P1 Jan. 2, 2014

(51) Int. Cl.
*A01H 5/00* (2006.01)

(52) U.S. Cl.
USPC ..... Plt./440

(58) Field of Classification Search
CPC ..... A01H 5/02; A01H 5/12
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by leaves which are colored rose to light plum, strongly veiled, and medium large, purple pink flowers on dark peduncles, a medium, mounding habit, excellent tolerance to heat and humidity, and good vigor.

1 Drawing Sheet

Botanical denomination: *Heuchera* hybrid.
Variety designation: 'Georgia Plum'.

BACKGROUND OF THE INVENTION

The present invention relates to a new and distinct cultivar of *Heuchera* and given the cultivar name of 'Georgia Plum'. *Heuchera* is in the family Saxifragaceae. *Heuchera* 'Georgia Plum' originated as a tissue culture mutation in *Heuchera* 'Georgia Peach' (U.S. Plant Pat. No. 19,375) and was found at the nursery production area in Canby, Oreg.

Compared to *Heuchera* 'Georgia Peach', the new cultivar has rose to light plum colored leaves rather than leaves that are pink-orange shades in the spring and early summer changing to burgundy-pink shades in the fall and winter. In addition the habit is more compact with shorter petioles. The flowers are purple pink rather than cream and are on shorter flowering stems.

Compared to *Heuchera* 'Plum Royale' (U.S. Plant Pat. No. 20,935), the new cultivar has flatter, duller leaves. The leaf color is rose to light plum rather than plum purple to silver.

This new *Heuchera* is uniquely distinguished by:

1. leaves which are colored rose to light plum, strongly veiled, and medium large,
2. purple pink flowers on dark peduncles,
3. a medium, mounding habit,
4. excellent tolerance to heat and humidity,
5. and good vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one and a half-year-old plant of *Heuchera* 'Georgia Plum' growing in a two gallon container, grown outside in April in Canby, Oreg.

FIG. 2 shows a plant of the same age growing in the trial beds in September in Canby, Oreg.

DETAILED PLANT DESCRIPTION

The following is a detailed description of the new *Heuchera* cultivar based on observations taken in mid-May of one and a half-year-old specimens growing in two gallon containers, grown outside in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, 5$^{th}$ edition.

Plant:

*Form.*—Basal rosette, herbaceous perennial.
*Hardiness.*—USDA Zone 4 to 9.
*Size.*—20 cm tall from top of the foliage to the ground and 42 cm wide.
*Habit.*—Mounding.
*Vigor.*—Good.

Leaf:

*Type.*—Simple.
*Arrangement.*—Rosette.
*Shape.*—Broadly ovate.
*Lobing/division.*—5 to 7 shallow lobes, the terminal the longest, shallow secondary lobes.
*Venation.*—Palmate.
*Margins.*—Crenate.

*Apex.*—Mucronulate.

*Base.*—Cordate, lobes overlapping at the base.

*Blade size.*—Grows to 15 cm long and 13 cm wide.

*Surface texture.*—Glandular on both sides.

*Petiole description.*—Grows to 15 cm long and 2.5 mm wide, glandular hairs, Greyed Purple 187B.

*Leaf color.*—Variable depending on season and age of the leaf, veins with strong colors and between the veins (interveinally) there is a heavy "silver" veil lightening the leaf color; topside, spring new leaves Greyed Purple N186D with the edges and veins Greyed Purple N186A, bottom side closest to Red Purple 59A all over; topside summer, fall and winter leaves Purple N77C with the edges and veins N77A, bottom side closest to Red Purple 59A all over.

Inflorescence:

*Size.*—Grows to 5 cm wide and 22 cm long.

*Type.*—Thyrse.

*Number of flowers per thyrse.*—About 50.

*Number of thyrse.*—About 10 in first spring flush.

*Peduncle.*—Grows to 25 cm long and 3 mm wide at base, Greyed Purple 187A, glandular hairs.

*Pedicel.*—Variable in size, with glandular hairs, Greyed Purple 187A.

*Bloom period.*—Heavy June bloom then occasional blooms May through October in Canby, Oreg.

Flower bud:

*Size.*—2.5 mm wide and 5 mm long.

*Description.*—Glandular puberulent, ovoid, down facing.

*Color.*—Red Purple 64A on bottom ⅔ and 64D on top ⅓.

Flower:

*Type.*—Perfect.

*Shape.*—Campanulate.

*Size.*—6.5 mm long and 4 mm wide.

*Corolla description.*—5 petals, 3 mm long and less than 1 mm wide, recurved, spatulate, margins entire, tip acute, glandular on topside and bottom side, Red Purple 70A on both sides.

*Calyx description.*—Campanulate, 6 mm long and 4 mm wide, with 5 lobes divided ½ way to the base, each 2 mm wide and 2.5 mm long, glandular on top and bottom, tip obtuse, margin entire; color both sides Greyed Purple 186C on bottom ⅓, Red Purple 73D on lobes and 64A on lobe tips.

*Stamen description.*—5 in number, filaments 3 mm long, White N155B, anthers 0.4 mm, Orange 26A, pollen Yellow Orange 22B.

*Pistil description.*—1, 2-beaked, 6 mm long and 1.8 mm wide, Red Purple 72C overall, ovary 2 mm long and 1.8 mm wide, style 4 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

We claim:

1. A new and distinct *Heuchera* plant as herein illustrated and described.

* * * * *

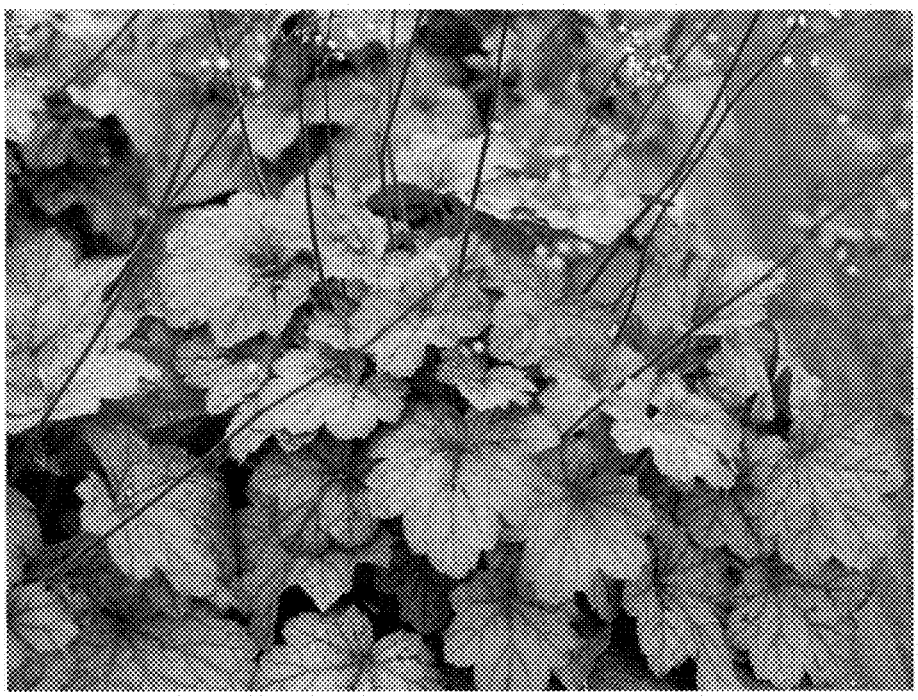

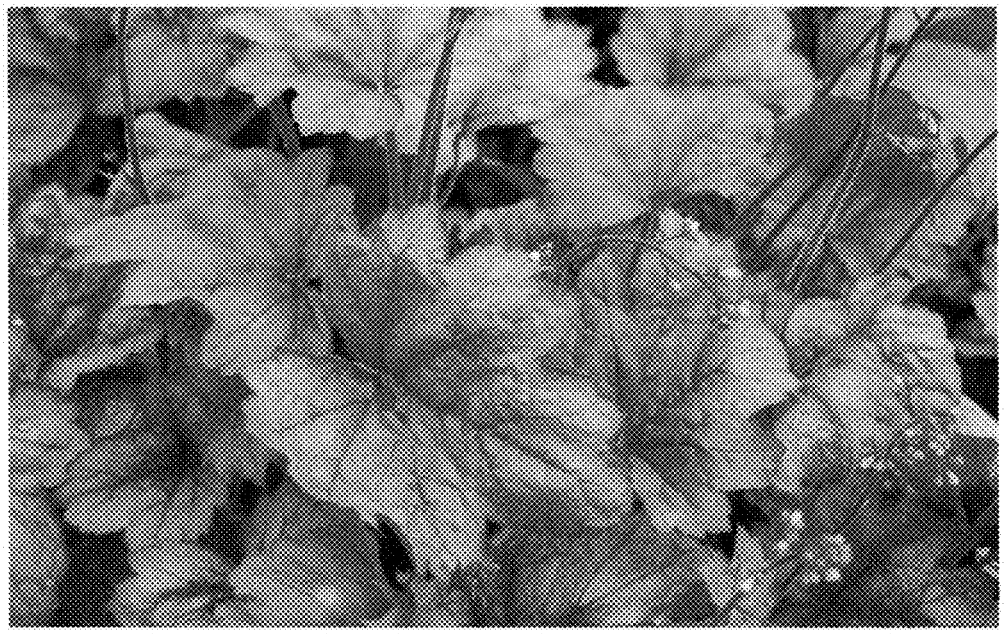
FIG. 1 above, FIG. 2 below